United States Patent [19]

Lay

[11] Patent Number: 4,686,355
[45] Date of Patent: Aug. 11, 1987

[54] OSTOMY APPLICATION DEVICE

[76] Inventor: Larry D. Lay, 26078 Alger, Madison Heights, Mich. 48071

[21] Appl. No.: 823,198

[22] Filed: Jan. 28, 1986

[51] Int. Cl.⁴ ............................................. H05B 3/22
[52] U.S. Cl. .................................. 219/385; 312/226; 108/33; 604/344; 219/201; 219/386; 219/218; 219/443; 219/521
[58] Field of Search ............... 219/200, 201, 385, 386, 219/219, 521, 217, 218, 443; 604/344; 108/33, 34, 35, 38, 41, 50; 312/226; 350/600, 632; 132/79 G, 80 A

[56] References Cited

U.S. PATENT DOCUMENTS

| | | | |
|---|---|---|---|
| 450,873 | 4/1891 | Rosenbaum | 108/50 |
| 2,471,884 | 5/1949 | Monnot | 219/218 |
| 2,733,110 | 1/1956 | Berner | 108/50 |
| 3,148,461 | 9/1964 | Johnson | 350/632 |
| 4,257,680 | 3/1981 | Baczkowski | 128/21 |

Primary Examiner—Clifford C. Shaw
Assistant Examiner—Teresa J. Walberg
Attorney, Agent, or Firm—Basile, Weintraub & Hanlon

[57] ABSTRACT

A collapsible mirror-heater unit for assisting in the application of ostomy pads is disclosed. A dual-faced mirror is pivotally mounted in a frame to expose either face and a heater is also pivotally mounted on the frame to be located in either of a stored or operative position. The device may be collapsed into its frame to provide a compact, box-like unit for storage.

4 Claims, 4 Drawing Figures

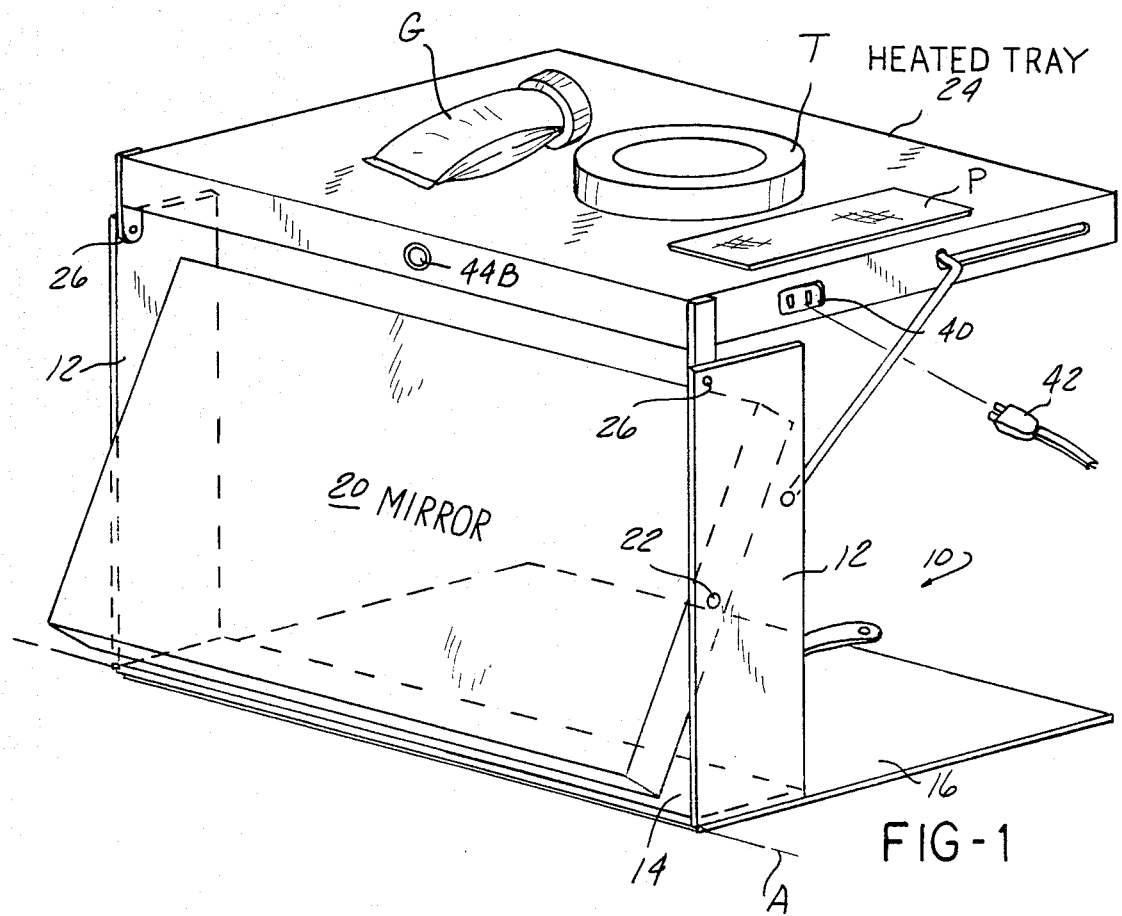
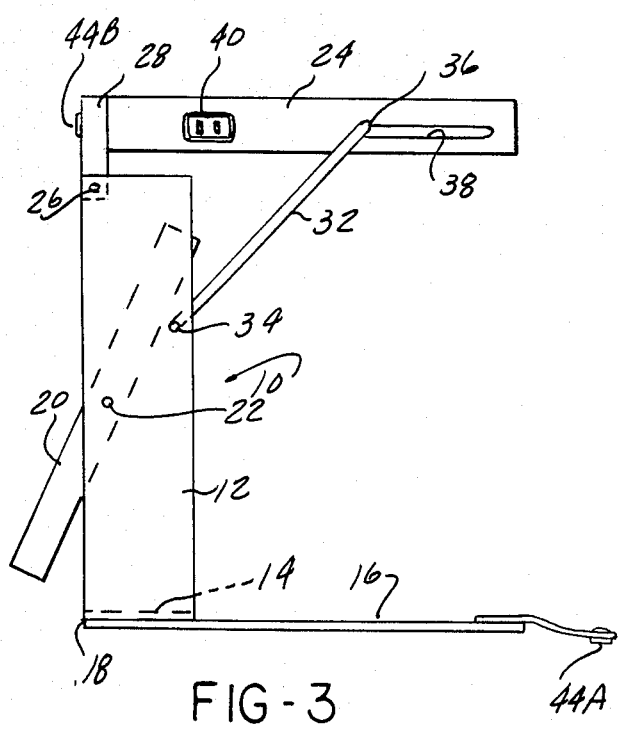
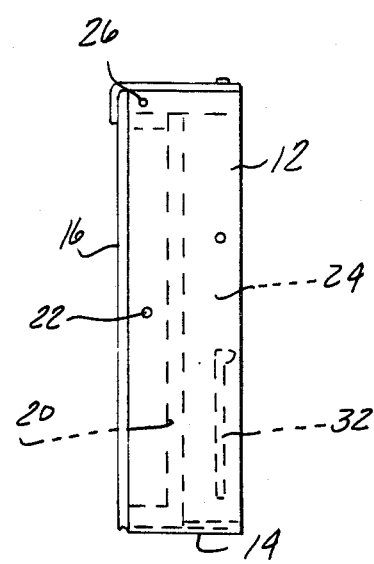

OSTOMY APPLICATION DEVICE

BACKGROUND OF THE INVENTION

The present invention is directed to a device for assisting ostomy patients in the replacement of ostomy pads.

An ostomy tube is surgically attached to a patient's intestine and let out through an opening surgically formed in the patient's skin to an externally located collection bag to drain the intestine in those cases where natural drainage is no longer possible. The surgical opening in the patient's skin through which the tube projects provides almost optimum conditions for the development of infection and it is necessary to maintain a sterile pad or bandage in position to shield this area. These pads require replacement on a daily basis.

The pad itself is formed with an opening which closely fits around the ostomy tube and is normally applied by first smearing the tube and surrounding skin area with a glue-like medical adhesive, placing the pad in position and then applying adhesive tape to seal the peripheral edges of the pad to the patient's skin.

The usual location at which the tube protrudes from the patient is roughly somewhere between the belt line and groin area and is thus somewhat difficult for the patient to view directly.

While the glue-like adhesive and the conventional tape will provide adequate adhesion when they are at room temperature, optimum adhesion, which is particularly important with the adhesive, will occur when the adhesive is at body temperature or slightly higher before it is applied.

The present invention is directed to a collapsible mirror-heater assembly which can be readily set up on a counter top to bring the various materials to the proper temperature and to provide a clear view of the area to which the pad is to be applied.

SUMMARY OF THE INVENTION

In accordance with the present invention, a rectangular mirror is mounted for pivotal movement about a horizontal axis passing centrally through the mirror between a pair of upright sidewall members which are interconnected at their lower ends by a bottom wall. The mirror is so mounted that, when it is in a vertical position, it is recessed between the two sidewall members near the front of the members. A rectangular heating element is pivotally mounted at its front edge to the sidewall members near the top of the members so that the heater can be swung from a collapsed or stored position recessed between the sidewalls to the rear of the mirror and a horizontal operating position in which the heater is supported above the sidewalls and projects rearwardly from them. A pair of rod-like brace members are each pivotally mounted at one end in one of the sidewalls, and each brace has its opposite end slidably received within an elongate slot, one slot being formed in each side of the heater element. An upwardly offset vertical notch at one end of each slot receives the end of the brace member to hold the heater in its horizontal operating position.

The unit may be provided with a front cover hingedly interconnected to the front edge of the bottom wall of the frame for hinging movement between a closed position in which the cover overlies the front of the mirror and a support position wherein the cover is hinged 270 degrees from its closed position to extend horizontally beneath the bottom wall of the frame and rearwardly of the frame to stabilize the unit when the heater is in its operating position.

Other objects and features of the invention will become apparent by reference to the following specification and to the drawings.

IN THE DRAWINGS

FIG. 1 is a perspective view of a mirror-heater unit embodying the present invention;

FIG. 3 is a side view of the device of FIG. 1; and

FIG. 4 is a side view of the device of FIG. 1 showing the various parts in their closed or storage position.

Figure 2:
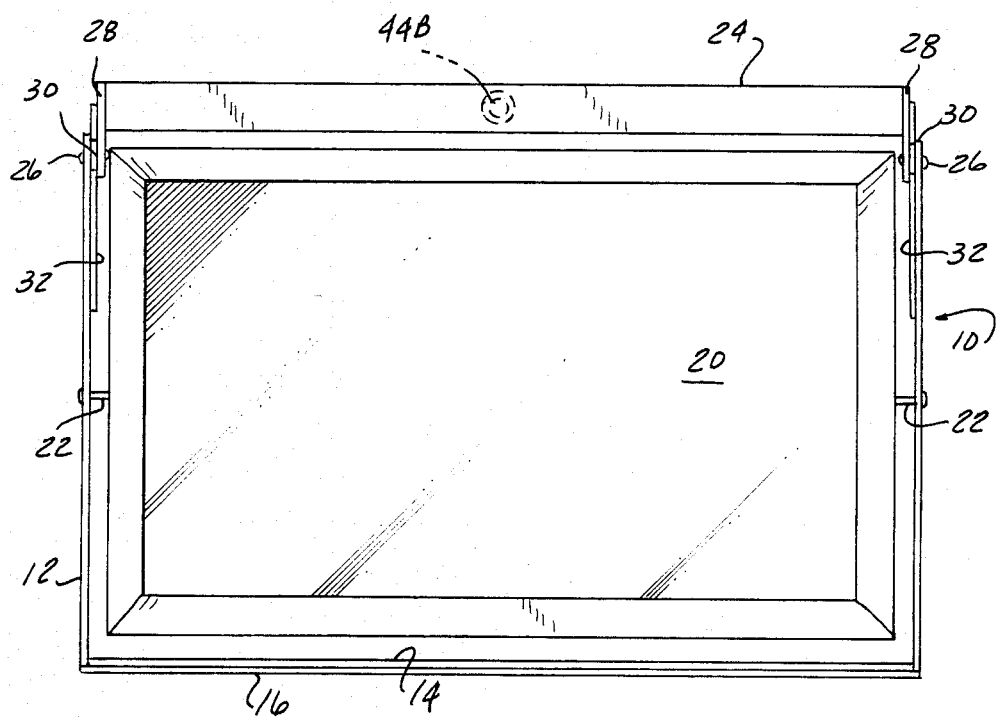
FIG. 2 is a front view of the device of FIG. 1.

As best seen in FIGS. 1 and 2, a collapsible mirror-heater unit embodying the present invention includes a frame designated generally 10 constituted by a pair of vertical sidewalls 12 fixedly interconnected to each other at their lower ends by a bottom wall 14. A flat, rectangular cover plate 16 is hingedly connected to the front edge of bottom wall 14 for hinging movement along an axis A (FIG. 1) which extends longitudinally along the front edge of the bottom wall. The frame 10 and cover plate 16 may be molded as an integral unit from a suitable plastic material with the hinged interconnection between plate 16 and bottom wall 12 constituted by a groove 18 (FIG. 3) or reduced thickness section. Alternatively, the cover plate and frame may be interconnected by a piano-type or other hinge capable of accommodating a 270-degree hinging movement beteen plate 16 and bottom wall 10 (compare FIGS. 3 and 4).

A mirror 20 is mounted between sidewalls 12 for pivotal movement about a horizontal axis passing centrally through the mirror as by pivot pins 22 rotatably received within bores in the sidewalls 12. Preferably, the mirror 20 is a double-faced mirror, one side being a conventional flat mirror and the other side having a curved surface which magnifies the image. In use, the mirror normally will be tilted, as illustrated in FIG. 1, and the pivots 22 are snugly received within the bores in sidewalls 12 to provide sufficient friction to hold the mirror at inclined positions of adjustment. Otherwise, the mirror may be rotated through 360 degrees so that either the plane or magnifying surface of the mirror will be exposed at the front of the device.

A generally rectangular, electrical heating element 24 is mounted for pivotal movement on pivots 26 located at the upper end of each sidewall 12. Arms 28 fixedly mounted at the front end of the heating element couple the heating element 24 to the pivots 26. As best seen in FIG. 2, spacers 30 are mounted on the pivots 26 to provide lateral clearance between the sides of the heating element 24 and sidewalls 12 to accommodate the location of rod-like braces 32 employed to hold the heating element in the operating position shown in FIGS. 1, 2 and 3.

Each of the rod-like brace members 32 is bent outwardly at one end 34 to be rotatably received within a bore in the respective sidewalls 12. The opposite end 36 of the brace 32 is bent 90 degrees in the opposite direction to project into an elongate slot 38 formed in each side of heating element 24. The inner or left-hand end of slot 38 as viewed in FIG. 3 is formed with an upwardly offset vertical extension 38a into which the end 36 of brace 32 is seated when the heater is in its operating position shown in FIG. 3. To release the heater from the operating position shown in FIG. 3, the right-hand end of heater element 24 is lifted slightly so that the end 36 of brace 32 engages the bottom of slot 38, at which time the heating element can be pivoted downwardly from the position shown in FIG. 3 with the end 36 of the brace members sliding outwardly to the right along slot 36 as the heater element swings from the operating position of FIG. 3 to the closed position of FIG. 4.

The heater is electically operated and a suitable socket, such as 40, is mounted in the heater to electrically connect the heating element to a mating plug 42 of an electric power cord partially illustrated in FIG. 1.

In FIGS. 1, 2 and 3, the unit is shown set up for operation. Typically, the unit will be set upon the top of a bathroom counter at approximately waist height. In FIG. 1, a tube of medical adhesive G, a roll of tape T and a stoma pad P are shown located on the heater which, when plugged in, will electrically heat these materials to a selected temperature which typically will be selected to be at or slightly above normal body temperature.

After use, the unit may be collapsed for storage by disengaging the braces 32 from the holding notch 38a at the inner end of slots 38 and pivoting the heater downwardly to the closed position shown in FIG. 4 in which the heater is recessed between sidewalls 12. The mirror, of necessity, will be swung to a vertical position as shown in FIG. 4. Cover plate 16 is then swung 270 degrees in a clockwise direction from that shown in FIG. 3 to the position shown in FIG. 4 where it will overlie the front face of mirror 20. A short strap with a snap or dot-type fastener 44A-44B may be employed to hold the cover 16 in the closed position shown in FIG. 4.

While one embodiment of the invention has been described in detail, it will be apparent to those skilled in the art the disclosed embodiment may be modified. Therefore, the foregoing description is to be considered exemplary rather than limiting, and the true scope of the invention is that defined in the following claims.

What is claimed is:

1. Apparatus for assisting in the application of an ostomy pad comprising a frame having a pair of upright frame members, a mirror mounted between said frame members for pivotal movement about an longitudinal axis, a tray-like heater, and means mounting said heater upon the upper ends of said frame members for pivotal movement between a collapsed, vertically disposed position between the frame members and an operative position wherein said heater is stably supported in a horizontal position adjacent the upper ends of said frame members and above the mirror.

2. The invention defined in claim 1 wherein said frame comprises a bottom wall and said upright frame members comprise a pair of sidewalls fixedly secured to and projecting vertically from the opposite ends of said bottom wall, said sidewalls having a front-to-rear dimension greater than the combined thicknesses of said mirror and said heater whereby said mirror and said heater may be nested between said sidewalls when said heater is in its collapsed position.

3. The invention defined in claim 2 wherein said mirror is of a rectangular configuration having a width less than the spacing between said sidewalls and a width less than the height of said sidewalls, said mirror including a pair of pivot pins located midway of the height of said mirror at opposite sides thereof respectively received in said sidewalls to accommodate a 360-degree rotation of said mirror relative to said frame about the axis of said pivot pins whereby either main surface of said mirror may be exposed at the front of said frame when said heater is in its operative position.

4. The invention defined in claim 3 wherein said heater is of rectangular configuration having a length less than the spacing between said sidewalls and a width substantially equal to the height of said sidewalls, pivot means mounting one longitudinal edge of said heater to said sidewalls at the upper ends thereof, brace means pivotally mounted at one end on each of said sidewalls, means defining an elongate slot in each side of said heater respectively slidably receiving the other end of said brace means, and means defining an offset portion at one end of each slot for receiving said one end of said brace means to releasably maintain said heater in its operative position.

* * * * *